US009872501B2

(12) United States Patent
Khanolkar et al.

(10) Patent No.: US 9,872,501 B2
(45) Date of Patent: Jan. 23, 2018

(54) METHODS FOR FORMING STABILIZED METAL SALT PARTICLES

(71) Applicant: Johnson & Johnson Vision Care, Inc., Jacksonville, FL (US)

(72) Inventors: Amit Khanolkar, Jacksonville, FL (US); Ture Kindt-Larsen, Holte (DK); Jens-Erik Sorensen, Hellerup (DK); Gerald L Yewey, St. Augustine, FL (US); Yongcheng Li, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/361,587

(22) Filed: Nov. 28, 2016

(65) Prior Publication Data
US 2017/0071211 A1 Mar. 16, 2017

Related U.S. Application Data

(62) Division of application No. 11/868,914, filed on Oct. 8, 2007, now abandoned.

(51) Int. Cl.
*C01G 9/00* (2006.01)
*A01N 59/16* (2006.01)
*A61L 12/08* (2006.01)
*G02B 1/04* (2006.01)

(52) U.S. Cl.
CPC ............ *A01N 59/16* (2013.01); *A61L 12/088* (2013.01); *C01G 9/006* (2013.01); *G02B 1/043* (2013.01); *C01P 2004/64* (2013.01); *C01P 2006/80* (2013.01); *C01P 2006/82* (2013.01)

(58) Field of Classification Search
CPC ............ C01B 31/24; C01G 9/00; C01G 9/006
USPC ...................................................... 423/419.1
See application file for complete search history.

(56) References Cited

U.S. PATENT DOCUMENTS

| | | | |
|---|---|---|---|
| 1,758,651 A | 5/1930 | Conover | |
| 1,788,334 A | 1/1931 | Schneider | |
| 2,040,806 A | 5/1936 | Feigi | |
| 2,072,809 A | 3/1937 | Bley | |
| 2,422,688 A | 6/1947 | Lott | |
| 2,689,609 A | 9/1954 | Fessler | |
| 2,853,414 A | 9/1958 | Wimmer | |
| 2,927,052 A | 3/1960 | Moudry | |
| 3,092,552 A | 6/1963 | Romans | |
| 3,637,391 A | 1/1972 | Saleck et al. | |
| 3,639,575 A | 2/1972 | Schmolka | |
| 4,229,360 A | 10/1980 | Schneider et al. | |
| 4,395,478 A | 7/1983 | Hoyen | |
| 4,579,731 A | 4/1986 | Fox, Jr. et al. | |
| 4,869,907 A * | 9/1989 | Sasagawa | A23K 40/20 424/442 |
| 5,019,096 A | 5/1991 | Fox, Jr. et al. | |
| 5,413,788 A | 5/1995 | Edwards et al. | |
| 5,707,552 A * | 1/1998 | Watanabe | B82Y 30/00 252/609 |
| 6,338,840 B1* | 1/2002 | Allan | A45D 40/16 264/102 |
| 6,605,751 B1 | 8/2003 | Gibbins et al. | |
| 6,716,895 B1 | 4/2004 | Terry | |
| 6,949,598 B2 | 9/2005 | Terry | |
| 7,179,849 B2 | 2/2007 | Terry | |
| 2003/0043341 A1 | 3/2003 | Turner et al. | |
| 2004/0116551 A1 | 6/2004 | Terry | |
| 2005/0013842 A1 | 1/2005 | Qiu et al. | |
| 2006/0141015 A1 | 6/2006 | Tessier et al. | |
| 2007/0003603 A1 | 1/2007 | Karandikar et al. | |
| 2007/0149427 A1 | 6/2007 | Minick | |
| 2007/0216298 A1 | 9/2007 | Terry | |

FOREIGN PATENT DOCUMENTS

| | | |
|---|---|---|
| EP | 0580179 B1 | 12/1998 |
| GB | 422948 A | 1/1935 |
| GB | 474614 A | 11/1937 |
| GB | 476376 A | 12/1937 |
| GB | 769799 A | 3/1957 |
| GB | 777670 A | 6/1957 |
| JP | 2007073431 A | 3/2007 |
| JP | 2007161649 A | 6/2007 |
| WO | 198201990 A1 | 6/1982 |
| WO | 200143788 A2 | 6/2001 |
| WO | 2002062402 A1 | 8/2002 |
| WO | 2003047636 A2 | 6/2003 |
| WO | 2004017738 A1 | 3/2004 |
| WO | 2004047878 A1 | 6/2004 |
| WO | 2005014074 A1 | 2/2005 |
| WO | 2005107455 A2 | 11/2005 |

OTHER PUBLICATIONS

Translation for JP 2007-073431, Mar. 2007.*
B.H.Carroll., Introduction to Photographic Theory, The Sliver Halide Emulsion, 1980, pp. 95-96.
Becker et al, The Use of High Accuracy NAA for the Certification of NIST Botanical Standard Reference Materials, Journal of Radioanalytical and Nuclear Chemistry, vol. 160, No. 1. 1992, pp. 41-53.
Becker et al, Use of INAA, PGAA, and RNAA to Determine 30 Elements for Certification of an SRM: Tomato Leaves, 1573a, Journal of Radioanalytical and Nuclear Chemistry, vol. 179, No. 1 (1994) pp. 149-154.
Brentano, et al., Antibacterial Efficacy of a Colloidal Silver Complex, Surgical Forum, 1966, pp. 76-78.
David R. Lide, Ph.D., AReady—Reference Book of Chemical and Physical Data, CRC Handbook of Chemistry and Physics, 1993, pp. 106-109, 78th Edition.
Encyclopedia of Polymer Science and Engineering, N-Vinyl Amide Polymers, Seocund Edition, Encyclopedia of polymer Science and Engineering, Second edition, pp. 198-257, vol. 17, 1989.

(Continued)

*Primary Examiner* — Ngoc-Yen Nguyen

(57) ABSTRACT

The present invention relates to a process for forming stabilized metal salt particles.

22 Claims, No Drawings

(56) References Cited

OTHER PUBLICATIONS

Ernest J. Perry, Extenctiometric Methods for Studying Protective Colloid Action and Oswald Ripening of Sliver Bromide Sols, Journal of Phys Chem, May 1958, pp. 585-589, vol. 62.

G. F. Duffin., Photographic Emulsion Chemistry, Photographic Emulsion Chemistry, 1966, pp. 1-30.

Guoping. et al., Preparation of dendritic silver nanoparticles by direct chemical reduction, 2005, pp. 1-8, vol. 7 Issue 1.

Henglein, et al., Photochemistry of Colloidal Semiconductors 30 Reactions and Fluorescence of AgI and AgI Ag,S Colloids, Ber. Bunsenges.Phys.Chem., 1959, pp. 593-599, vol. 93.

Hidefumi Hirai, Formation and Catalytic Functionality of Synthetic Polymer-Noble Metal Colloid, J.Macromol. Sci-Chem., 1979, pp. 633-549, vol. A13 Isuue 5.

Hirai, et al., Interactions of poly(N-vinyl-2-pyrrolidone) with colloidal copper particles, Markromol.Chem.,Rapid Couuun., 1984, pp. 381-384, vol. 5.

Hoppe, et al., One-Step Synthesis of Gold and Silver Hydrosols Using Poly(N-vinyl-2-pyrrolidone) as a Reducing Agent, Langmuir, May 30, 2006, pp. 1-8.

Huang, et al., Photochemical Formation of Silver Nanoparticles in Poly(N-vinylpyrrolidone), Langmuir, 1996, pp. 909-912, vol. 12.

I.B.Romans, A.B., Silver Conipounds, Lea & Febiger, 1954, pp. 380-387.

Jack G. Calvert., The Utilization of the Solar Energy Through Photochemical Reactions, The Ohio Journal of Science, Sep. 1953, pp. 293-299, vol. 53 Issue 5.

James T.H., The Theory of Photographic Process, The Theory of Photographic Process, Fourth Edition, 1980, pp. 95-96.

Kim, et al., Role of anions for the reduction behavior of silver ions in polymer/silver salt complex membranes, Journal of Membrane Science, 2005, pp. 207-214, vol. 250.

Kowalik, et al., Use of dacron vascular prosthesis impregnated with salts of silver, in treatment of extraanatomical axilla-femoral bi-pass infection. infections in vascular surgery, Polimery w Medycynie, 2002, pp. 80-84, p. No.

Luvitec, Selected Examples and possible uses in technical applications, Luvitec, pp. 1-4.

Masaaki Sugiura., Research on Synthetic Polymer Photographic Emulsions (1st Report) Electrophoretic Mobility of Polyvinyl Pyrrolidone in Buffer Solution, Tokyo Industrial Laboratory Report, May 29, 1967, pp. 411-415, vol. 62 Issue 11.

Melaiye, et al., Silver and its application as an antimicrobial agent. Expert Opin. Ther. Patents, 2005, pp. 125-130, vol. 15 Issue 2.

Milton Wruble., Colloidal Silver Sulfonamides, Journal of the American Pharmaceutical Association, 1943, pp. 80-82, p. No.

N.Grier., Silver and its Compounds in Disinfection Sterilization and preservation, Philadelphia LEA & Febiger, 1983, pp. 375-389, 3rd Edition.

Qian, et al., Preparation and characterization of polyvinylpyrrolidone films containing silver sulfide nanoparticles, Journal of Materials Chemistry, Sep. 10, 2001, pp. 2504-2506, vol. 11.

Russel, et al., Colloidal Dispersions, Collodial Dispersions, 1989, pp. 12-14 : 162-210.

Sambhy, et al., Silver Bromide Nanoparticle/Polymer Composites: Dual Action Tunable Antimicrobial Materials, Journal of American Chemical Society, Jul. 7, 2006, pp. 1-11, p. EST : 10.4.

Wang, et al., Preparation of silver nanoparticles by chemical reduction method, Colloids and Surfaces A: Physicochem. Eng. Aspects, Jan. 30, 2005, pp. 111-115, vol. 256.

Zhang, et al., PVP Protective Mechanism of Ultrafine Silver Powder Synthesized by Chemical Reduction Processes, Journal of Solid State Chemistry, 1996, pp. 105-110, vol. 121.

* cited by examiner

METHODS FOR FORMING STABILIZED METAL SALT PARTICLES

RELATED APPLICATIONS

This application is a division of U.S. patent application Ser. No. 11/868,914 filed Oct. 8, 2007, currently pending; entitled METHODS FOR FORMING STABILIZED METAL SALT PARTICLES, the contents of which are incorporated by reference.

FIELD OF THE INVENTION

This invention relates to methods for forming stabilized metal salt particles.

BACKGROUND OF THE INVENTION

Processes for forming colloidal solutions and powders of silver (0) stabilized by polyvinyl pyrollidone (PVP) have been disclosed. In the first step of these processes PVP has been mixed with silver nitrate to form a PVP-silver ion complex. The silver ion is then reduced with agents such as hydrazine hydrate or glucose and sodium hydroxide. A process which uses the PVP-silver ion complex to for stabilized metal salt particles is not disclosed.

SUMMARY OF THE INVENTION

The present invention relates to methods for forming stabilized metal salt particles. Specifically the present invention relates to a process comprising
a. forming a first solution comprising at least one salt precursor;
b. forming a second solution comprising a complex formed from at least one metal agent and at least one dispersing agent in a particle size stabilizing effective amount;
c. adding said second solution to said first solution to form a clear product solution comprising stabilized metal salt particles having an average particle size of less than about 200 nm;
d. drying said product solution to form an antimicrobial metal salt powder comprising 0.01 to about 10 weight % metal in the antimicrobial metal salt powder.

The stabilized metal salt particles may be added to a wide variety of polymers, either in the reactive mixture or in a compounding step. In one embodiment the metal salt particles are antimicrobial, and impart antimicrobial properties to the polymer to which they are added.

DETAILED DESCRIPTION OF THE INVENTION

As used herein, the term, "antimicrobial" means that the article exhibits one or more of the following properties, the inhibition of the adhesion of bacteria or other microbes to the article, the inhibition of the growth of bacteria or other microbes on article, and the killing of bacteria or other microbes on the surface of the article or in an area surrounding the article. For purposes of this invention, adhesion of bacteria or other microbes to the article, the growth of bacteria or other microbes on lenses and the presence of bacterial or other microbes on the surface of article are collectively referred to as "microbial colonization." Preferably, the articles of the invention exhibit at least about 0.25 log reduction, in some embodiments at least about 0.5 log reduction, and in some embodiments at least about a 1.0 log reduction (≥90% inhibition) of viable bacteria or other microbes. Such bacteria or other microbes include but are not limited to *Pseudomonas aeruginosa, Acanthamoeba* species, *Staphyloccus. aureus, E. coli, Staphyloccus epidermidis,* and *Serratia marcesens*.

As use herein, the term "metal salt" means any molecule having the general formula $[M^{q+}]_a[X^{z-}]_b$ wherein X contains any negatively charged ion, a, b, q and z are independently integers ≥1, $q(a)=z(b)$. M may be any positively charged metal ion selected from, but not limited to, the following $Al^{+3}, Cr^{+2}, Cr^{+3}, Cd^{+1}, Cd^{+2}, Co^{+2}, Co^{+3}, Ca^{+2}, Mg^{+2}, Ni^{+2}, Ti^{+2}, Ti^{+3}, Ti^{+4}, V^{+2}, V^{+3}, V^{+5}, Sr^{+2}, Fe^{+2}, Fe^{+3}, Au^{+2}, Au^{+3}, Au^{+1}, Ag^{+2}, Ag^{+1}, Pd^{+2}, Pd^{+4}, Pt^{+2}, Pt^{+4}, Cu^{+1}, Cu^{+2}, Mn^{+2}, Mn^{+3}, Mn^{+4}, Zn^{+2}, Se^{+4+2}$ and mixtures thereof. In another embodiment, M may be selected from $Al^{+3}, Co^{+2}, Co^{+3}, Ca^{+2}, Mg^{+2}, Ni^{+2}, Ti^{+2}, Ti^{+3}, Ti^{+4}, V^{+2}, V^{+3}, V^{+5}, Sr^{+2}, Fe^{+2}, Fe^{+3}, Au^{+2}, Au^{+3}, Au^{+1}, Ag^{+2}, Ag^{+1}, Pd^{+2}, Pd^{+4}, Pt^{+2}, Pt^{+4}, Cu^{+1}, Cu^{+2}, Mn^{+2}, Mn^{+3}, Mn^{+4}, Se^{+4}$ and $Zn^{+2}$ and mixtures thereof. Examples of X include but are not limited to $CO_3^{-2}, NO_3^{-1}, PO_4^{-3}, Cl^{-1}, I^{-1}, Br^{-1}, S^{-2}, O^{-2}$, acetate, mixtures thereof and the like. Further X includes negatively charged ions containing $CO_3^{-2}, SO_4^{-2}, PO_4^{-3}, Cl^{-1}, I^{-1}, Br^{-1}, S^{-2}, O^{-2}$, acetate and the like, such as $C_{1-5}alkylCO_2^{-1}$. In another embodiment, X may comprise $CO_3^{-2}, SO_4^{-2}, Cl^{-1}, I^{-1}, Br^{-1}$, acetate and mixtures thereof. As used herein the term metal salts does not include zeolites, such as those disclosed in US-2003-0043341-A1. This patent application is hereby incorporated by reference in its entirety. The preferred a is 1, 2, or 3. The preferred b is 1, 2, or 3. The preferred metals ions are $Mg^{+2}, Zn^{+2}, Cu^{+1}, Cu^{+2}, Au^{+2}, Au^{+3}, Au^{+1}, Pd^{+2}, Pd^{+4}, Pt^{+2}, Pt^{+4}, Ag^{+2},$ and $Ag^{+1}$ and mixtures thereof. The particularly preferred metal ion is $Ag^{+1}$. Examples of suitable metal salts include but are not limited to manganese sulfide, zinc oxide, zinc carbonate, calcium sulfate, selenium sulfide, copper iodide, copper sulfide, and copper phosphate. Examples of silver salts include but are not limited to silver carbonate, silver phosphate, silver sulfide, silver chloride, silver bromide, silver iodide, and silver oxide. In one embodiment the metal salt comprises at least one silver salt such as silver iodide, silver chloride, and silver bromide.

For embodiments where the stabilized metal salt is to be incorporated into an article in contact with water miscible solutions, including water miscible bodily fluids like blood, urine, tears or saliva, and antimicrobial efficacy of greater than about 12 hours is desired, the metal salt has a $K_{sp}$ of less than about $2 \times 10^{-10}$ in pure water at 25° C. In one embodiment the metal salt has a solubility product constant of not more than about $2.0 \times 10^{-17}$ moles/L.

As used herein, the term "pure" refers to the quality of the water used as defined in the CRC Handbook of Chemistry and Physics, 78$^{th}$ Edition, CRC Press, Boca Raton Fla., 1993. Solubility-product constants ($K_{sp}$) measured in pure water at 25° C. for various salts are published in CRC Handbook of Chemistry and Physics, 78$^{th}$ Edition, CRC Press, Boca Raton Fla., 1993) For example, if the metal salt is silver carbonate ($Ag_2CO_3$), the $K_{sp}$ is expressed by the following equation $$Ag_2CO_3(s) \rightarrow 2Ag^+(aq) + CO_3^{2-}(aq)$$

The $K_{sp}$ is calculated as follows $$K_{sp} = [Ag^+]^2[CO_3^{2-}]$$

As silver carbonate dissolves, there is one carbonate anion in solution for every two silver cations, $[CO_3^{2-}] = \frac{1}{2}[Ag^+]$, and the solubility-product constant equation can be rearranged to solve for the dissolved silver concentration as follows $$K_{sp}=[Ag^+]^2(\frac{1}{2}[Ag^+])=\frac{1}{2}[Ag^+]^3$$

$$[Ag^+]=(2K_{sp})^{1/3}$$

The term "salt precursor" refers to any compound or composition (including aqueous solutions) that contains a cation that may be substituted with metal ions. It is preferred that the salt precursor is soluble in selected solvent at about 1 μg/mL or greater. The term does not include zeolites as described US2003/0043341 entitled "Antimicrobial Contact Lenses and Methods of Use," or activated silver as described in WO02/062402, entitled "Antimicrobial Contact Lenses Containing Activated Silver and Methods for Their Production". Examples of salt precursors include but are not limited to inorganic molecules such as sodium chloride, sodium iodide, sodium bromide, lithium chloride, lithium sulfide, sodium sulfide, potassium sulfide, sodium tetrachloro argentate, mixtures thereof and the like. Examples of organic molecules include but are not limited to tetra-alkyl ammonium lactate, tetra-alkyl ammonium sulfate, tetra-alkyl phosphonium acetate, tetra-alkyl phosphonium sulfate, quaternary ammonium or phosphonium halides, such as tetra-alkyl ammonium chloride, tetra-alkyl phosphonium chloride, bromide or iodide, and the like. In one embodiment the precursor salt comprises sodium iodide.

The salt precursor solution is formed by dissolving the salt precursor in at least one solvent. The concentration of salt precursor in the salt precursor solution is desirably at least about at least about 1500 ppm up to the solubility limit for the salt precursor in the selected solvent, in some embodiments between about 5000 ppm and the solubility limit and in some embodiments between about 5000 ppm and about 50,000 ppm (5 wt %) and in other embodiments between about 5000 and about 20,000 ppm (2 wt %).

The term "metal agent" refers to any composition (including aqueous solutions) containing metal ions. Examples of such compositions include but are not limited to aqueous or organic solutions of silver nitrate, silver triflate, silver acetate, silver tetrafluoroborate, copper nitrate, copper sulfate, magnesium sulfate, zinc sulfate, mixtures thereof and the like.

The metal agent solution is formed by dissolving the metal agent in at least one solvent. The concentration of metal agent in the metal agent solution is desirably at least about at least about 1500 ppm up to the solubility limit for the metal agent in the selected solvent, in some embodiments between about 5000 ppm and the solubility limit, in some embodiments between about 5000 ppm and 50,000 ppm (5 wt %) and in other embodiments between about 5000 and about 20,000 ppm (2 wt %). Suitable solvents (a) dissolve the metal agent, salt precursor and dispersing agent, (b) do not reduce the metal agent to metal and (c) can be readily removed by known methods. Water, alcohols or mixtures thereof may be used. Suitable alcohols are capable of solubilizing the metal agent and salt precursor. When silver nitrate and sodium iodide are used as the metal agent and salt precursor, alcohols such as t-amyl alcohol, tripropylene glycol monomethyl ether, and mixtures thereof and mixtures with water may be used. Water may also be used alone.

At least one of the metal agent solution and the salt precursor solution further comprises at least one dispersing agent, and in one embodiment, the metal agent mixture further comprises at least one dispersing agent. Suitable dispersing agents include polymers which comprise functional groups with lone pair electrons. Examples of dispersing agents include hydroxyalkylmethylcellulose polymers, polyvinyl alcohol, polyvinyl pyrrolidone, polyethylene oxide, polysaccharides, such as starch, pectin, gelatin; polyacrylamide, including polydimethylacrylamide, polyacrylic acid, organoalkoxysilanes such as 3-aminopropyltriethoxysilane (APS), methyl-triethoxysilane (MTS), phenyltrimethoxysilane (PTS), vinyl-triethoxysilane (VTS), and 3-glycidoxypropyltrimethoxysilane (GPS), polyethers, such as polyethylene glycol, polypropylene glycol, boric acid ester of glycerin (BAGE), silicone macromers having molecular weights greater than about 10,000 and comprising groups which increase viscosity, such as hydrogen bonding groups, such as but not limited to hydroxyl groups and urethane groups and mixtures thereof.

In one embodiment the dispersing agent is selected from the group consisting of hydroxyalkylmethylcellulose polymers, polyvinyl alcohol, polyvinyl pyrrolidone, polyethylene oxide, glycerin, boric acid ester of glycerin (BAGE), gelatin and polyacrylic acid, and mixtures thereof. In another embodiment the dispersing agent is selected from the group consisting of hydroxypropylmethylcellulose, polyvinyl alcohol, polyvinyl pyrrolidone, polyethylene oxide, gelatin, glycerin and BAGE and mixtures thereof. In yet another embodiment the dispersing agent is selected from the group consisting of polyvinyl alcohol, polyvinyl pyrrolidone, and polyethylene oxide, and mixtures thereof.

Where the dispersing agent is a polymer, it can have a range of molecular weights. Molecular weights from about 1000 up to several million may be used. The upper molecular weight limit is bounded only by the solubility of the dispersing agent in the metal salt mixture, the salt precursor mixture and the reactive mixture. For glycoside polymers such as gelatin and methyl cellulose the molecular weight may be above a million. For non-glycoside polymers like polyvinyl alcohol, polyvinyl pyrrolidone and poly acrylic acid, the molecular weight may range from about 2,500 to about 2,000,000, in some embodiments from about 10,000 to about 1,800,000 Daltons, and in other embodiments from about 20,000 to about 1,500,000 Daltons. In some embodiments molecular weights of greater than about 50,000 Daltons may be used, as dispersing agents in this range provide better stabilization in some polymer systems.

Alternatively, the molecular weight of the dispersion-stabilizing polymers can be also expressed by the K-value, based on kinematic viscosity measurements, as described in Encyclopedia of Polymer Science and Engineering, N-Vinyl Amide Polymers, Second edition, Vol 17, pgs. 198-257, John Wiley & Sons Inc. When expressed in this manner, non-glycoside dispersing agent polymers may have K-values from about 5 to about 150, in some embodiments from about 5 to about 100, from about 5 to about 70 and in other embodiments from about 5 to about 50.

Stabilized metal salt nanoparticles may be formed by forming a salt precursor solution comprising at least one salt precursor;

forming a metal agent solution comprising a complex formed from at least one dispersing agent having a weight average molecular weight of at least about 1000 and at least one metal agent;

adding one solution to the other at a rate sufficient to maintain a clear solution throughout addition and to form a product solution comprising stabilized metal salt nanoparticles having a mean particle size of less than about 50 nm; and drying said stabilized salt nanoparticles.

Any of the dispersing agents described above may be used. The dispersing agent is included in either or both the metal agent and salt precursor solutions, or can be included in a third solution, into which the metal agent and salt precursor solutions are added. In embodiments where both the salt precursor solution and metal agent solutions comprise at least one dispersing agent, the dispersing agents may be the same or different.

The dispersing agent is included in an amount sufficient to provide a particle size of less than about 500 nm ("particle size stabilizing effective amount"). In embodiments where the clarity of the final article is important, the particle size is less than about 200 nm, in some embodiments less than about 100 nm, and in others still, less than about 50 nm. In one embodiment, at least about 20 weight % dispersing agent, is used in at least one solution to insure that the desired particle size is achieved. In another embodiment, between about 20 and about 50 weight % dispersing agent is used. In some embodiments the molar ratio of dispersing agent unit to metal agent is at least about 1.5, at least about 2, and in some embodiments at least about 4. As used herein, dispersing agent unit is a repeating unit within the dispersing agent. In one embodiment the metal agent solution comprises dispersing agent. In some embodiments it will be convenient to have the same concentration of dispersing agent in both solutions.

The upper concentration limit for dispersing agent in the solutions may be determined by solubility of the dispersing agent in the selected solvent, and ease of handling of the solutions. In one embodiment, each solution has a viscosity of less than about 50 cps. In one embodiment the product solution may have up to about 50 weight % dispersing agent. As described above, the metal agent and salt precursor solutions may have the same or different concentrations of dispersing agent. All weight % are based upon the total weight of all components in the solution.

The mixing of the solutions may be conducted at room temperature, and may beneficially include stirring. Stirring speeds at or above which a vortex is created may be used. The selected stirring speed should not cause frothing, foaming or loss of solution from the mixing container. Stirring is continued throughout addition.

Mixing may be conducted at ambient pressure, or decreased pressure. In some embodiments, mixing may cause the solution to froth or foam. Foaming or frothing is undesirable as it may cause pockets of higher concentration of the metal salt to form, which results in larger than desired particle size. In these cases decreased pressure may be used. The pressure can be any pressure between ambient and the vapor pressure for the selected solvent. In one embodiment, where water is the solvent, the pressures may be between ambient and about 40 mbar.

The rate of addition of the salt precursor and metal agent solutions is selected to maintain a clear solution throughout mixing. Slight localized haze may be acceptable so long as the solution clears with stirring. Clarity of the solution may be observed visually or monitored using UV-VIS spectroscopy. Suitable addition rates may be determined by preparing a series of solutions having the desired concentration, and monitoring the clarity of the solution at different addition rates. This procedure is exemplified in Examples 2-7. Including dispersing agent in the salt precursor solution may also allow for faster rates of addition.

In another embodiment, where faster addition rates are desired, the metal agent and dispersing agent are allowed to mix under complex-forming conditions, including a complex-forming time before mixing with the salt precursor solution. It is believed that the dispersing agent in the metal agent solution forms a complex with the metal agent. In this embodiment, it is desirable to allow the metal agent to fully complex with the dispersing agent prior to combining the metal agent solution and the salt precursor solution. "Fully complexed" means that substantially all the metal ions have complexed with at least one dispersing agent. "Substantially all" means at least about 90%, and in some embodiments at least about 95% of said metal ions have complexed with at least one dispersing agent.

The complex-forming time may be monitored in solution via spectroscopy, such as via UV-VIS or FTIR. The spectra of the metal agent solution without the dispersing agent is measured. The spectra of the metal agent solution is monitored after addition of the dispersing agent, and the change in spectra is monitored. The complex-forming time is the time at which the spectral change plateaus.

Alternatively, complexation time may be measured empirically by forming a series of metal agent-dispersing agent solutions having the same concentration, allowing each solution to mix for a different time (for example 1, 3, 6, 12, 24, 72 hours and 1 week), and mixing each metal agent-dispersing agent solution batch-wise with the salt precursor solution. The metal agent-dispersing agent solutions which are mixed for complex-forming times will form clear solutions when the metal agent and salt precursor solutions are poured together directly without controlling the rate of addition. For example, 20 ml of metal agent solution may be added to 20 ml of salt precursor solution in 1 second or less.

Complexation conditions include complexation time (discussed above), temperature, ratio of the dispersing agent to the metal agent and stirring rates. Increasing the temperature, molar ratio of dispersing agent to metal agent and stirring rate, will decrease complexation time. Those of skill in the art will, with reference to the teachings herein, can vary the conditions to achieve the disclosed complexation levels.

If the metal agent and dispersing agent are not fully complexed, the mixing conditions may be selected to bias reactions in the mixture to forming the dispersing agent-metal agent complex over the formation of uncomplexed metal salt. This biasing may be achieved by controlling the (a) concentration of dispersing agent in the salt precursor, or the solution into which the salt precursor and metal agent solutions are added and (b) rate of mixing of the metal agent and salt precursor solutions.

Once the metal agent and salt precursor solutions have been mixed, the nanoparticle-containing product solution may be dried. Any conventional drying equipment may be used such as freeze dryers, spray dryers and the like. Drying equipment and processes are well known in the art. An example of a suitable spray dryer is a cyclone spray dryer, such as those available from GEA Niro, Inc. For spray drying the temperature of the spray inlet is above the flash point for the selected solvent.

Freeze dryers are available from numerous manufacturers, including GEA Niro, Inc. Freeze drying temperatures and pressures are selected to sublimate the solvent as is well known by those of skill in the art. Any temperature within conventional ranges for the method selected may be used.

The product solution is dried until the resulting powder has a solvent content of less than about 10 weight %, in some embodiments less than about 5 weight % and in some embodiments less than about 2 weight %. Higher solvent concentrations may be appropriate where the solvent used to form the stabilized metal salt is compatible with the reaction mixture used to form the polymeric article. The powder is a stabilized metal salt nanoparticle having a particle size of up to about 100 nm, up to about 50 nm, and in some embodiments up to about 15 nm as measured by as measured by transmission electron microscopy or dynamic light scattering by dispersing in water.

The stabilized metal salt powder may be added directly to polymeric reaction mixtures, or compounded with thermoplastic polymers, which can then be used to form polymeric coatings. The stabilized metal salt powder may also be added to a wide variety of coating formulations. The amount of stabilized metal salt powder to be added may be readily calculated to provide the desired level of functionality. For example, where the metal salt is antimicrobial, the amount of metal salt powder added to the bulk polymer or coating formulation may be readily calculated to provide the desired level of antimicrobial metal ion.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

Particle size was measured using laser light scattering or dynamic light scattering. For samples with a particle size range greater than about 500 nm a Horiba-LA930 laser diffraction particle size analyzer was used. The instrument check was performed from the blank % T values. One mL of the sample solution was introduced into the circulation bath which contained 150 mL of water as medium. A relative refractive index of 1.7-0.1 i and a circulation speed of 5 was used. The samples were ultrasonicated for two minutes prior to measurement using ultrasonication in the instrument. Triton® X-100 (commercially available from Union Carbide) (0.1%) was used as a surfactant in the analysis. Triplicate analysis was performed and the traces were compared to make sure that they coincided with each other. The instrument provided a report containing a graph of the particle size distribution along with values for the mean particle size.

For samples with a particle size range less than about 500 nm a Malvern 4700 dynamic light scattering apparatus was used. The instrument check was performed prior to analysis of the samples using NIST traceable standard size polystyrene particles. One ml of the sample was diluted to 20 ml with water and the samples were sonicated for one minute using Branson Ultrasonic probe and both relative refractive index and viscosity values were entered in the software. The instrument provides a report containing a graph of the particle size distribution along with values for the mean particle size.

EXAMPLES

Example 1: Formation of AgI Nanodispersion

Metal agent and salt precursor solutions were formed as follows: 10,000 ppm $AgNO_3$ was dissolved with stirring in 200 gm of a 50 w/w % solution of PVP K12 in DI water. NaI (10,000 ppm) was dissolved with stirring in 200 gm of a 50 w/w % solution of PVP K12 in DI water. The metal salt solution containing $AgNO_3$ was added to the salt precursor solution at a rate of 200 gm/hour with stirring at 2013 rpm. The metal salt solution was spray dried in air. The inlet temperature was 185° C., the outlet temperature was 90° C. and the feed rate was 2.7 kg/hr. The stabilized AgI nanoparticles had a water content of less than 5 weight %.

Examples 2-4

A 100,000 ppm solution of PVP K12 was made in DI water. This solution (solution A) provided the base for making NaI and $AgNO_3$ solutions. Solutions of approximately 1500 ppm, 5000 ppm and 10000 ppm of each of NaI and $AgNO_3$ were made. Each solution was stirred until no visible particles were observed. A 20 mL portion of NaI solution was placed in a clean jar and magnetic stirrer was placed inside. The stirrer was set at 300 rpm and 20 ml. of $AgNO_3$ was added to the NaI solution at the rate shown in Table 1, below. All mixing was conducted at ambient temperature. The haze of the solution was subjectively assessed at the end of the listed addition time and results are reported in Table 1, below. The Example was repeated for each concentration and addition rate shown in Table 1.

TABLE 1

| Addn rate (ml/sec) | Addn Time (sec) | Ex 2 1500 ppm | Ex 3 5000 ppm | Ex 4 10,000 ppm |
|---|---|---|---|---|
| 20 | 1 | clear | milky | Milky |
| 4 | 5 | clear | Mild haze | Milky |
| 2 | 10 | clear | clear | Mild haze |
| 1 | 20 | clear | clear | Clear |
| 0.67 | 30 | clear | clear | Clear |

Examples 5-7

Examples 2-4 were repeated, except that the NaI solution was added to the $AgNO_3$ solution. The results are shown in Table 2, below.

TABLE 2

| Addn rate (ml/sec) | Addn Time (sec) | Ex 5 1500 ppm | Ex 6 5000 ppm | Ex 7 10,000 ppm |
|---|---|---|---|---|
| 20 | 1 | clear | milky | Milky |
| 4 | 5 | clear | milky | Milky |
| 2 | 10 | clear | milky | Milky |
| 1 | 20 | Clear | Milky | Mild haze |
| 0.67 | 30 | Clear | Clear | Clear |

Example 8

Example 7 was repeated, except that the metal agent and salt precursor solutions were mixed for about ~5 days, and then batch-wise mixed (poured together in about 1 second). The result was a clear silver iodide solution.

Examples 9-15

Approximately 10 mL of 700 ppm $AgNO_3$ solution was formed in PVP K12:DI water solution at the PVP concentrations shown in Table 3 (1% to 35% PVP K12 in DI water). Each $AgNO_3$ solution was dropwise-added to 10 mL of 1100 ppm NaI/DI solution (no PVP) with manual shaking to form dispersions. Example 9 was milky. The remaining Examples remained clear throughout addition of the $AgNO_3$. Particle size measurements were carried out on the resulting AgI dispersions using laser light scattering (Examples 9) and photon correlation spectrophotometry (Examples 10-15). Data is reported as z-average of the particle size distribution

TABLE 3

| Ex# | [PVP K12] (wt %) | Particle Size (nm) |
| --- | --- | --- |
| 9 | 0% | 10600 |
| 10 | 1% | 270 |
| 11 | 2% | 40 |
| 12 | 10% | 540 |
| 13 | 15% | 400 |
| 14 | 25% | 40 |
| 15 | 35% | 20 |

The data in Table 3 clearly shows that the presence of PVP during metal salt formation decreases particle size substantially (at least two orders of magnitude).

Examples 16-19

Example 10 was repeated, except the dispersing agents listed in Table 4 were used instead of PVP, and at the concentrations listed in Table 4. Particle size measurements were carried out on the resulting AgI dispersions using laser light scattering (16, 17 and 19) and photon correlation spectrophotometry (18, 20). Data is reported as z-average of the particle size distribution.

TABLE 4

| Ex# | Dispersing agent | Particle Size (nm) |
| --- | --- | --- |
| 16 | 5% PAA 2K | 2760 |
| 17 | 5% PEO 10K | 7020 |
| 18 | 10% PEO 10K | 475 |
| 19 | GLYCERIN | 6380 |
| 20 | PVA 120K | 470 |

We claim:

1. A process comprising
   a. forming a first solution comprising at least one carbonate salt precursor;
   b. forming a second solution comprising a complex formed from at least one zinc metal agent and at least one dispersing agent in a particle size stabilizing effective amount;
   c. adding said second solution to said first solution at a rate sufficient to maintain a clear solution throughout addition and to form a product solution comprising stabilized metal salt particles having a mean particle size of less than about 200 nm;
   d. drying said product solution to form $Zn(CO_3)_2$ antimicrobial metal salt powder comprising 0.01 to about 10 weight % Zn in the antimicrobial metal salt powder.

2. The process of claim 1 wherein said second solution has a metal agent concentration of at least about 1500 ppm.

3. The process of claim 1 wherein the dispersing agent is present in said second solution in a concentration between about 20 and about 50 w/w %.

4. The process of claim 1 wherein said first solution has a salt precursor concentration of at least about 1500 ppm.

5. The process of claim 1 wherein said first solution has a salt precursor concentration of at least about 5000 ppm.

6. The process of claim 1 wherein said first solution has a salt precursor concentration of about 5000 ppm to about 50,000 ppm.

7. The process of claim 1 wherein said mean particle size is less than about 100 nm.

8. The process of claim 1 wherein said mean particle size is less than about 50 nm.

9. The process of claim 1 wherein said first and second solutions are aqueous solutions.

10. The process of claim 1 wherein said product solution has a viscosity of less than about 50 cps.

11. The process of claim 1 wherein said first solution is stirred as said second solution is added.

12. The process of claim 9 wherein said solutions are maintained at a pressure between about ambient and about 40 mbar during said adding step.

13. The process of claim 1 wherein said dispersing agents are independently selected from the group consisting of hydroxyalkylmethylcellulose polymers, polyvinyl alcohol, polyvinyl pyrrolidone, polyethylene oxide, starch, pectin, polyacrylamide, gelatin, polyacrylic acid, organoalkoxysilanes 3-aminopropyltriethoxysilane, methyltriethoxysilane, phenyltrimethoxysilane, vinyltriethoxysilane, 3-glycidoxypropyltrimethoxysilane, boric acid ester of glycerin and mixtures thereof.

14. The process of claim 1 wherein at least one of said first and second solution comprises at least one solvent and said powder comprises less than about 10 wt % of said solvent.

15. The process of claim 14 wherein said powder comprises less than about 5% of said solvent.

16. The process of claim 14 wherein said solvent comprises water.

17. The process of claim 14 wherein said metal agent comprises at least one silver salt which is soluble in said at least one solvent.

18. The process of claim 13 wherein said dispersing agent comprises polyvinyl pyrrolidone.

19. The process of claim 18 wherein said polyvinyl pyrrolidone and metal agent are present in said second solution in a molar ratio of at least about 1.5.

20. The process of claim 1 wherein said metal salt powder comprises at least one metal salt having a $K_{sp}$ of less than about $2 \times 10^{-10}$ in pure water at 25° C.

21. The process of claim 1 wherein said second solution has a metal agent concentration of at least about 5000 ppm.

22. The process of claim 1 wherein said second solution has a metal agent concentration of about 5000 ppm to about 50,000 ppm.

* * * * *